United States Patent [19]

Lazarus

[11] Patent Number: 4,523,909
[45] Date of Patent: Jun. 18, 1985

[54] PLASTIC DENTAL MATRIX AND METHOD OF MANUFACTURING SAME

[76] Inventor: Harry J. Lazarus, 36 Knox La., Englishtown, N.J. 07726

[21] Appl. No.: 586,569

[22] Filed: Mar. 6, 1984

[51] Int. Cl.³ ............................................. A61C 5/04
[52] U.S. Cl. ..................................................... 433/39
[58] Field of Search ............................ 433/141, 39, 40

[56] References Cited

U.S. PATENT DOCUMENTS

3,421,222  1/1969  Newman ............................... 433/39

Primary Examiner—Robert Peshock
Attorney, Agent, or Firm—McGlew and Tuttle

[57] ABSTRACT

A dental matrix for engaging around a tooth comprises a plastic sheet member which is preferably transparent and includes a straight winding portion connected to a curved tooth engaging portion. The gingivally recessed straight windable portion is wound into a coil and heat treated to retain a desired inside and outside diameter for the coil. A first end of the straight windable portion which is disposed in the interior of the coil is provided with a metal laminate, ridges or a clip for permitting engagement with a winding tool for further winding and tightening the cylindrical coil, to adapt the matrix to the tooth. A second end of the sheet member which is carried by the curved tooth engaging portion has lock-loop recesses or extrudedly rimmed apertures for receiving a metal lock-loop which is thus fixed to the second head end member and slidably receives an intermediate portion of the member which is between the coil and the second end. This forms the curved tooth engaging portion into a band for engagement around a tooth and permits a sliding drawing of the intermediate portion with respect to the second head end of the sheet member for tightening and locking of the band around the tooth.

33 Claims, 35 Drawing Figures

PLASTIC DENTAL MATRIX AND METHOD OF MANUFACTURING SAME

FIELD AND BACKGROUND OF THE INVENTION

The present invention relates in general to dental matrices for engaging around a tooth, and in particular to a new and useful dental matrix made primarily of plastic material and requiring no external retainer for retaining the matrix on a tooth.

Retainerless dental matrices are known from the Inventor's previous U.S. Pat. Nos. 3,411,214 granted Nov. 19, 1968 and 3,921,299 granted Nov. 25, 1975. These all-metal matrices utilize a cylindrical coil which can be engaged by a specially designed Dentist's coil winding tool for winding the coil against a lock loop to tighten and lock a band portion of the matrix around a tooth to be restored. These locked on matrices permit removal of the winding tool from the matrix, and the mouth. Thus this matrix is retainerless.

The winding tool is disclosed by the Inventor's U.S. Pat. Nos. 3,435,905 granted Apr. 1, 1969 and 3,852,884 granted Dec. 10, 1974.

Other types of dental matrices which require external retainers are also known from U.S. Pat. Nos. 606,420 to Ivory and 2,538,486 to Tofflemire. Said retainers project from Patient's mouth, blocking vision and cluttering the operative field.

Dental matrices of the type which must be tightened around a tooth have been made of metal due to the fact that a metal matrix band can be made sufficiently thin to fit in a space between the teeth while at the same time having sufficient strength to accommodate the forces necessary to firmly engage and lock on a tooth. The metal for dental matrices is usually maleable and work-hardenable stainless steel. The matrix is placed completely around the prepared tooth to be reconstructed or restored and then held tightly to the tooth by any of several retaining mechanisms. Filling material is then placed at appropriate locations in or on the tooth and allowed to harden. After this the band is removed. The filling material has conventionally been amalgam alloy or composite restorative materials consisting of hardenable resin which contains organic or inorganic fillers.

Various dental restorative materials are now known and widely utilized which are curable by visible or ultraviolet light. While utilizing such light-curable restorative materials in combination with the known metal matrices, which are opaque, presents an undesirable barrier to the beam of curing light when it is time to cure the restorative material. While a thin layer of restorative material is visible from the open occlusal area of the matrix can be cured by the light, composite material at and below the gingiva, proximal and floor of the tooth cannot be readily exposed to the light.

Some examples of light handenable restorative material are the restorative products sold under the tradename of NUVA-FIL which can be cured by ultraviolet light. More recently restorative material has been developed which can be cured by visible light such as those sold under tradenames of PRISMA-FIL and FUL-FIL. NUVA-FIL, PRISMA-FIL and FUL-FIL are tradenames for these restorative products which are produced by the L. D. Caulk Co. of Milford, Del.

SUMMARY OF THE INVENTION

The present invention is drawn to a plastic dental matrix which can be utilized as a retainerless matrix with a windable cylindrical coil and which, being plastic can be transparent for permitting transmission of light to all surfaces of a tooth for the hardening of light curable restorative material.

The invention is also drawn to various mechanisms for distributing and absorbing the forces which must be exerted on the retainerless matrix by a Dentist's winding tool for a tight locked-on engagement around the tooth.

While the retainerless plastic matrix of the invention has the new advantages of permitting the transmission of light and utilizing less expensive material, the previous advantages of a retainerless dental matrix such as that disclosed by the Inventor's U.S. Pat. No. 3,921,299, are also retained by new and novel means hereinafter disclosed. These advantages include the capacity for the plastic matrix to engage and lock tightly around the sub-gingival circumference of the tooth sufficiently tight to resist restorative material from escaping sub-gingivally through an otherwise loosely fitted matrix. Said escape would have the undesirable effect of causing gingival recession adjacent the tooth being restored.

Accordingly an object of the present invention is to provide a dental matrix for engaging around a tooth which comprises a plastic sheet or blanked film member having a straight windable portion carrying a first end or tail end of the sheet or film blank member, and a curved tooth engaging portion carrying a second end of the sheet member. The straight windable portion is wound into a cylindrical coil having a plurality of windings, with the coil being heat treated to retain a desired inside and outside diameter required for engagement of Dentist's winding and tightening tool. The first end of the sheet member is disposed within the coil and provided with winder engaging means to permit engagement of the interior of the coil with a Dentist's winding tool. The second end of the member which is carried by the curved tooth engaging portion includes at least one "U" shaped recess and one aperture for engaging a locking means which also slidably receives an intermediate portion of the member lying between the coil and the second head end of the member. By engaging the coil with said winding tool and winding the coil the intermediate portion withdraws all surplus banding material and winds it onto the enlarging coil to tighten the curved tooth engaging portion, now formed into a matrix band, around a tooth to be restored. The lock-loop means is shaped and positioned to automatically lock the matrix and prevent loosening of the matrix band after the Dentist's winding tool is removed from the coil and the mouth.

A further object of the invention is to provide an anti-coning mechanism for preventing interior coil windings from telescopically moving toward and projecting into the gingiva of a patient being treated with the matrix, when the Dentist's winding tool is inserted into the coil.

A still further object of the invention is to provide a method of manufacturing a plastic dental matrix wherein the coil is held in its wound state by heat treating the coil during manufacture. Heat can be applied to the coil by a heated mandril used for the original winding of the coil, or by a heated external member engaging around a portion of the coil, or by hot air applied externally to the coil.

To improve the retension and strength of the engagement between the locking member and the second end of the plastic matrix member, one or two receiving means or apertures for engaging the locking member may be made of thicker material or be reinforced by extruding the edges only around the periphery of the aperture or apertures.

A metal strip laminated to the first or the first and second ends of the plastic sheet member may be utilized to form the winder engaging means or reinforce the receiving means in the second head end for engaging the locking means. The use of a metal laminate at the first tail end to form the winder engaging means also provides internal springyness to the coil to permit coil to expand, after tightening the matrix, this benefits easy withdrawal of the winding tool once the coil is wound against the lock-loop, and the matrix is locked on the tooth.

A still further object of the invention is to provide a plastic dental matrix which is simple in design and rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 21 is a view similar to FIG. 20 of another embodiment of the winding head, having an anti-coning O-ring;

FIG. 22 is a perspective view of another form of the heated A-symmetrical coil forming mandril for forming the coil;

FIG. 23 is a top plan view of a coil wound by the mandril of FIG. 22;

FIG. 24 is a sectional view taken along line 24—24 of FIG. 22;

FIG. 25 is a front plan view of another embodiment of the matrix, having a gingival anti-coning tapered tail end;

FIG. 26 is a view similar to FIG. 25 of a still further embodiment of the matrix;

FIG. 27 is a transverse sectional view taken through a tooth adjacent its gingiva engaged by the inventive matrix with the matrix fully tightened around the tooth, but unlocked due to a lack of coil-to-lock-loop contact;

FIG. 27a is a view similar to FIG. 27 showing that proper coil-to-lock-loop contact occurs only when a steel laminated endge is under the lock-loop, rather than beyond the lock-loop, as in FIG. 27 (lock is activated only when the laminate is as in FIG. 27a and FIG. 4);

FIG. 28 is a partial perspective exploded view of the matrix coil, with the band wrapped around the tooth and about to be engaged and tightened by a Dentist's winding tool which is shown only in part; and FIG. 29 is an exploded perspective view showing how a portion of the matrix and locking loop can be cut to open and remove the matrix from a tooth, and showing the lower section of the lock-loop remaining engaged in the gingival positioned lock-loop aperture, in matrix head, (cut segment is captured in enclosure of a lock-loop cutting instrument not shown).

DESCRIPTION OF THE PREFERRED EMBODIMENTS

Figures 1, 2:
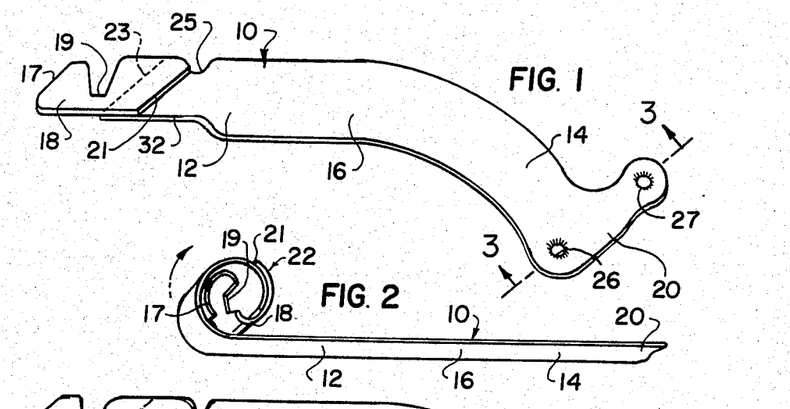
FIG. 1 is a front plan view of a plastic film matrix blank sheet member for forming the matrix of the invention.
FIG. 2 is a fragmentary perspective view of the matrix shown in FIG. 1 with the coil partially formed.

Referring to the drawings in particular, the invention embodied in FIG. 1 comprises a dental matrix having a plastic sheet member 10 with a straight windable portion or tail 12 adapted to be wound into a winding and tightening coil and a curved tooth engaging portion 14. The sheet member 10 also includes an intermediate portion 16 which is a non-coiled segment of straight portion 12 which, as will be explained in greater detail hereinunder, is slidably drawn through the lock-loop for enabling the tightening and locking of the tooth engaging curved band portion around a tooth, as in FIG. 8a, when coil is fully wound.

According to the embodiment of FIG. 1, a first end carried by the tail 12 is formed of metal sheet material which is laminated to the tail by adhesive or any other appropriate mechanism. The plastic film of the blank sheet member 10, can for example be made of PVC or co-polyester film or any other suitable transparent or opaque plyable, work handenable material, such as for example cellophane or celluloid material having a thickness of about 0.004 inches with a preferred thickness being on the order of 0.0015 to 0.002 inches, here referred to as plastic film. This roughly corresponds to the thickness of metal matrix material which must be thin enough to be insertable between the teeth. The metal laminate material forming end 18 can advantageously be 304 stainless steel which is work handenable. Terminal portion of end 18 does not have plastic undermetal beyond dot-line 23. This metal end has advantages in providing a desirable springyness to the interior of the coil as will be explained later. The metal laminate may preferably be on order of 0.0015 to 0.003 inches thick.

Figures 13, 14, 14A, 15, 16, 17, 18, 18A, 19, 20, 21A:
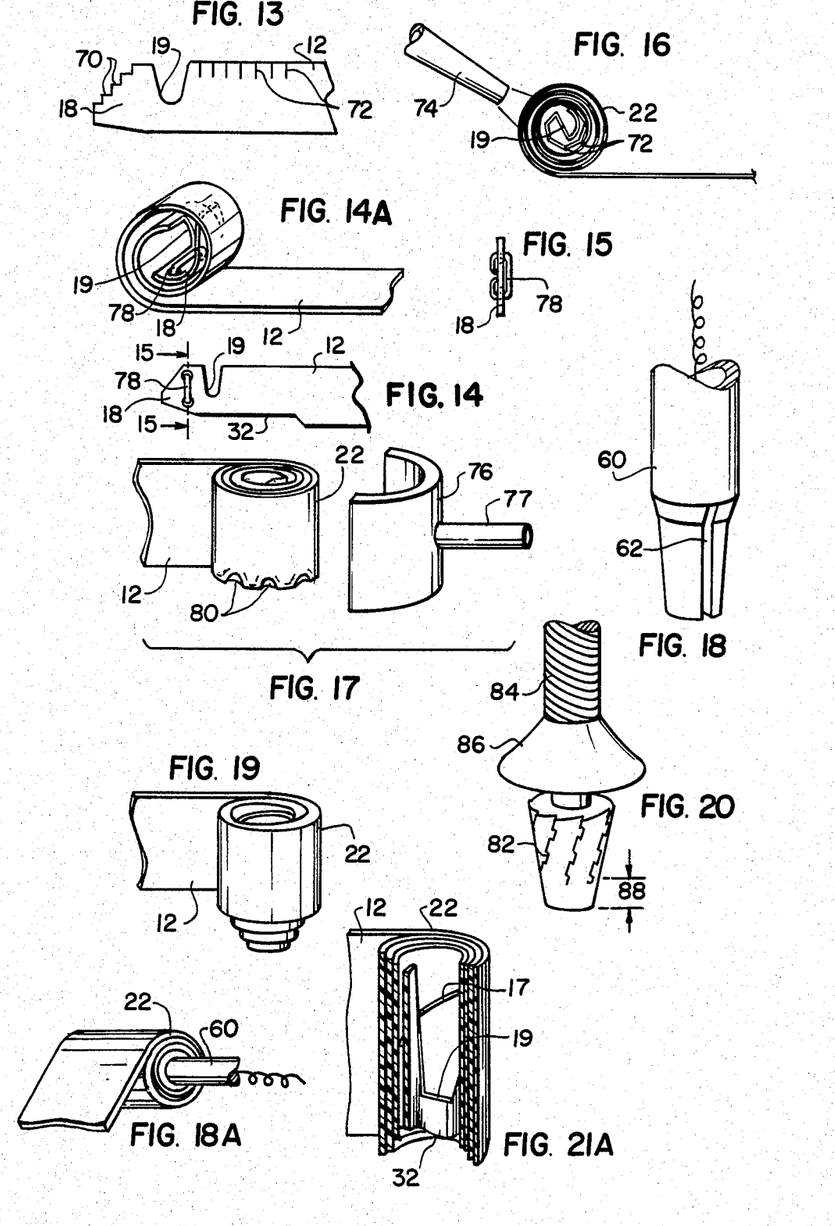
FIG. 13 is a fragmentary front plan view of the straight windable portion of a matrix according to another embodiment of the invention.
FIG. 14 is a view similar to FIG. 13 of a still further embodiment of the invention.
FIG. 14a is a perspective view of the windable portion of FIG. 14 in its coiled state.
FIG. 15 is a view taken along line 15—15 of FIG. 14.
FIG. 16 is a top plan view of the embodiment of FIG. 13 showing also a forced hot air method for heating the coil for retaining its shape and its inner and outer dimensions.
FIG. 17 is an exploded view illustrating another method of heating the coil and also illustrating a heat created anti-coning dimpled means for preventing telescopic displacement of inner windings of the coil toward the gingiva of a patient.
FIG. 18 is a partial perspective view of a heated mandril having dual diameters which is usable to form and set the coil's dimensions with dual-core coning-resistant, core diameters.
FIG. 18a is a view showing the heated coiling mandril of FIG. 18, forming coil 22.
FIG. 19 is a fragmentary perspective view showing a plastic coil which has telescoped gingivally upon entry of a dentist's winding tool so that said cone would project into the gingiva of a patient.
FIG. 20 is a fragmentary perspective view of the winding head of a dentist's winding tool which can be used to wind the coil of the invention and having an anti-coning shoulder thereon.
FIG. 21a is a sectioned view of a formed cylindrical coil showing the winder engaging means, internally of said coil core.

The first end 18 has a notch 19 for engagement by a dual-diametered, heated winding mandril 60 illustrated in FIG. 18 for example. In FIG. 1, the plastic material of tail 12 is overlaped by the metal material of end 18 between an edge 21 of the metal material and an edge 23 (shown in dotted line) of the plastic material. Edge 21 is at an acute angle with respect to a longitudinal axis of tail 12 to improve the distributional forces between the dissimilar materials. To avoid any sharp projecting edges which might cause injury to a patient, all the edges of first end 18 are rounded. In addition a recess 25 is defined in the top edge of tail 12 which blends into the top edge of first end 18, and is thereby non-projecting outwardly from the coil.

In FIG. 1, a rear edge 17 of metal first end 18 is also disposed at an angle with respect to a longitudinal axis of the tail 12 to facilitate engagement of edge 17 with teeth of a Dentist's winding tool tip 82 illustrated in FIG. 20.

The head or second end 20 of blank sheet member 10, in the embodiment of FIG. 1, is made entirely of plastic and includes lock-loop retaining means in the form of a pair of extruded apertures 26,27. As illustrated in FIG. 28, these apertures receive an upper and lower part of a locking loop, examples of which are shown in FIGS. 6, 7, 8 and 8a, said lock-loops having impregnators 90, as in FIG. 28, which bites into plastic band 16, when coil bears against said lock-loop.

Figures 3, 4, 5, 6, 7, 8, 8A:
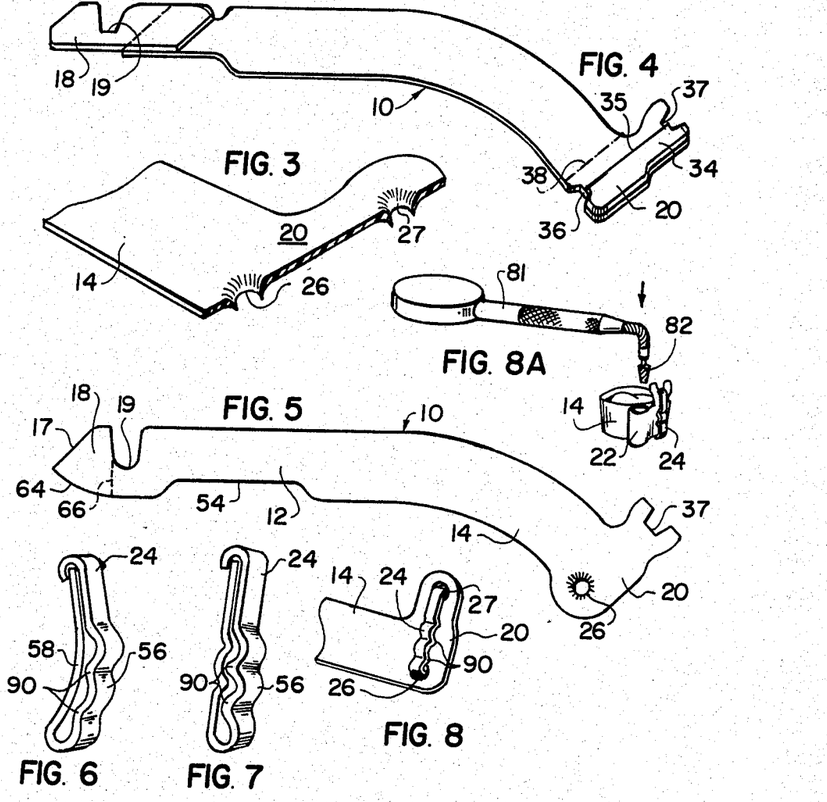
FIG. 3 is a fragmentary sectional view taken along line III—III of FIG. 1 showing extruded rimmed apertures.
FIG. 4 is a view similar to FIG. 1 of another embodiment of the invention having two laminated end portions.
FIG. 5 is a view similar to FIG. 1 of a still further embodiment of the invention.
FIG. 6 is a perspective view of a locking loop for holding the matrix in the form of a band in locked engagement around a tooth, said loop legs being in arcuate form.
FIG. 7 is a view similar to FIG. 6 of another embodiment of the lock-loop.
FIG. 8 is a fragmentary view of a FIG. 6 lock-loop affixed in receiving apertures of a plastic matrix blank.
FIG. 8a is a perspective view of a dentist's winding tool about to enter a coil in the invented matrix band, with said matrix in its assembled form and seated on a tooth, with said winding tool about to be used to wind the coil to tighten and lock the matrix on the tooth.
Figure 9:
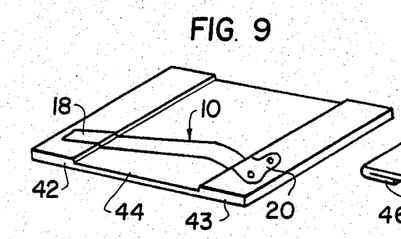
FIG. 9 is a perspective view of a blank plastic sheet from which inventive matrices can be die stamped, having thickened end portions.
Figure 10:
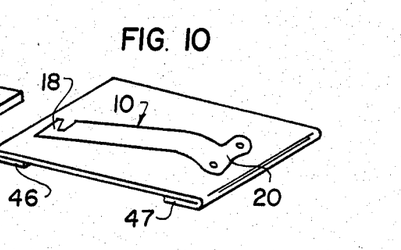
FIG. 10 is a view similar to FIG. 9 of another embodiment of the plastic blank sheet material with thickened end portions.

The extruded apertures 26,27 of FIGS. 1 and 3 are rounded with inward rolled edges rather than having tearable square or linear edges to better distribute forces exerted on the plastic edges of the apertures by the engaged locking loop 24 and the forces to be exerted by the lock-loop. To absorb lock-loop shearing forces, and referring to FIG. 3, the rolled-in extruded edges of the apertures are essentially thicker than the remaining portion of head 20. This can be provided by stamping apertures in a combined punching and extrusion manner by utilizing a conically round punch which is slightly smaller in diameter than the die for receiving said punch. Accordingly, the punch does not provide clean cut aperture. Rather, instead, the punch pierces and then extrudes the edges of the pierced material into the die hole, thereby extruding film through to the opposite side of the plastic film's aperture, with the result that a lip or rim is thereby created to resist the tearing forces that the lock-loop applies to the aperture during the winding of the coil against the lock-loop. Another way of thickening the area surrounding the apertures 26, is to thicken the entire head or second end 20. This can be done by using sheet material as a blank sheet to form the matrix of the invention as illustrated in FIGS. 9 and 10. In FIGS. 9 and 10, both the first and second ends of the matrix are provided with thicker plastic. In the embodiment of FIG. 9, an all plastic matrix is shown made from a sheet having thicker edges 42,43 and a thinner intermediate or center portion 44. An outline of the matrix generally designated 10 is also shown with its first end 18 and its second end 20, thickened.

It is noted that throughout the figures the same reference numerals are utilized to designate the same of similar parts in the various embodiments.

In FIG. 10, the thickened first and second ends are obtained by folding under edges of the plastic sheet at 46 and 47. Said folded ends may be cemented into position.

Figures 11, 12:
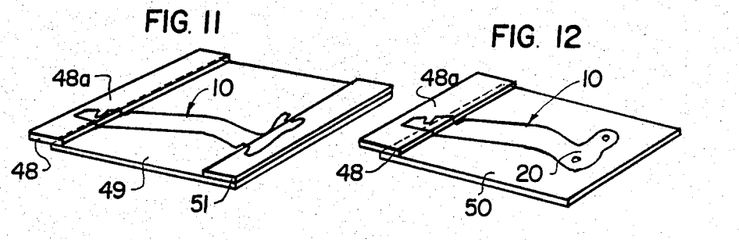
FIG. 11 is a view similar to FIG. 9 having a plastic central film sheet portion and a pair of metal end strip laminates for stamping the matrix illustrated in FIG. 4.
FIG. 12 is a view similar to FIG. 11 of a blank sheet for stamping the matrix blank illustrated in FIG. 1.
Figures 12A, 12B:
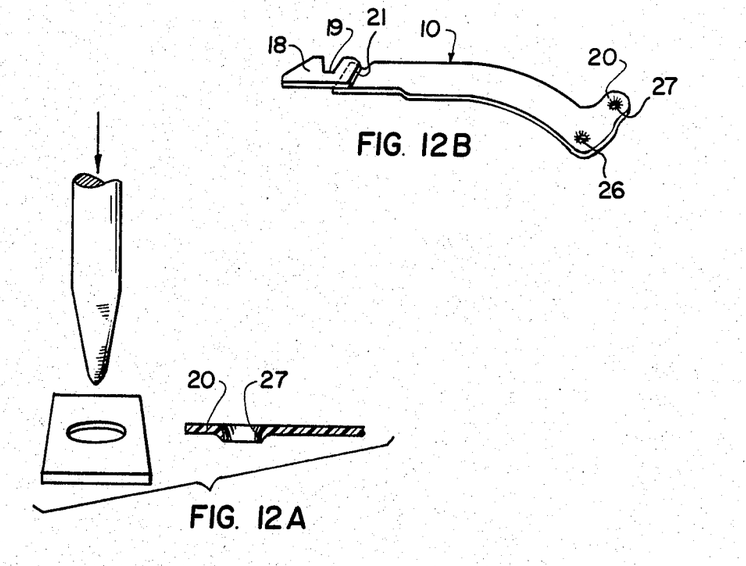
FIG. 12a is a perspective explanatory view of a conical, pointed punch shown over an oversized die hole for piercing and extruding a rimmed aperture for lock-loop engagement.
FIG. 12b is a plan view of a die stamped blank from the sheet of FIG. 12.

The embodiment of the matrix shown in FIG. 1 having a metal laminate at the end 18 can be manufactured by using a blank sheet illustrated in FIG. 12. A plastic sheet 50 is connected to a metal strip 48. Note the angle between a lower edge of the sheet 50 and the outline of the matrix 10 which sets the angles of edges 21 and 23 shown in FIG. 1. Also note that the plastic film does not extend to the terminal end of metal portion 18, as seen in FIGS. 1 and 12b. This metal-only portion 48a at end 18, provides a springyness to end 18 which facilitates disengagement of the dentist's winding tool after tool has tightened the coil and matrix band to the tooth.

Referring to FIG. 2, after the flat matrix of FIG. 1 is die stamped, its tail or straight windable portion 12 is wound into a coil which is shown partly wound by general disignation 22. Winding is achieved by engaging notch 19 in metal laminated end 18, with the slot 62 of a heated winding mandril 60 illustrated in FIG. 18. Said heated mandril having dual diameters through its length which when forming said coil creates a dual diametered anti-coning, non-telescopic coil. The wound portion of first tail end 18 having notch 19 as shown in FIG. 2 forms a "cross hair" through the center of the coil. As in FIG. 21a the elevation of notch 19 is sufficiently deep into coil core so that when the coil is engagable by a Dentist's winding tool, the winding tool enters coil sufficiently to engage the edge 17, as shown in FIG. 28. As also shown in FIG. 2, the coil winding is conducted clockwise from the coil's occlusal opening so that edge 18 extends counter-clockwise. In the fully wound coil shown in FIG. 27 for example a plurality of plastic film windings wind around the exterior of the metal end 18 and 18a. The coil is set by heating the coil during manufacture. The heating also causes some plastic to deform against the edge 21 (FIG. 1) of the laminated end 18 to improve the vertical stability of the coil and prevent a coning effect which is illustrated in FIG. 19. Note, FIG. 18a shows heated mandril 60 forming said coil.

As coning of the coil may more readily occur in a plastic coil, several anti-coning means must be employed. Another mechanism for avoiding the coning effect shown in FIG. 19 is by providing a gingival recess 32 at the first tail end of the tail 12. In this way the first tail end 18 is narrower in width than the remainder of the tail 12 so that there is less tendency for internal coil windings produced by the first end to be telescopically pushed against the gingiva of a patient, during the tightening of the coil. Additionally, heat being employed to set the coil's diameters also creates anti-coning dimples 80, as in FIG. 17, where internal recess 32 as in FIG. 1, permits the outer windings of the coil to shrink somewhat against said inner recess area to create said anti-coning dimples or curved outer edge to the coil.

The embodiment of FIG. 4 has several features similar to the embodiment of FIG. 1, particularly in the first end area. A major difference in the embodiment of FIG. 4 however is in the use of a metal laminate 34 at the head or second end 20. Also, the recess means rather than being apertures 26,27 are recessed notches 36,37. To effect the locking of the matrix on the tooth, the coil 22, must be wound up against the lock-loop and against the impregnators 90, of lock-loop 24, as seen in FIG. 28. Top and bottom portions of the locking loop engage over and under the notches 36,37. It is noted that to enable contact of coil against the lock-loop the metal laminate 34 extends only to an intermediate location on the notches 37. It is important to avoid extending the laminate 34 to the dot-line 38, as such would defeat lock-loop function. Also, if the laminate 34 is narrower so that it doesn't cover at least a portion of the notches 36,37 there is insufficient strength in the head and the notches can be torn away from the remainder of the matrix, when coil and matrix is tightened on a tooth.

The reason for avoiding extending the metal laminate 34 to the dot-line 38 is illustrated in FIG. 27. In FIG. 27, the coil 22 is shown fully wound. As the coil is being wound, it draws material in the direction of arrow 45. The intermediate portion 16 of the sheet member 10 is slidably drawn through the lock-loop 24, causing coil 22 to increase in diameter from receiving more material which is being slidably drawn in the direction of arrow 45, towards the winding enlarging coil, to activate the lock-loop's locking action, at point 52 the coil must bear against the lock-loop while being wound. However, if the metal laminate were to extend to dot-line 38, said coil would stop its advance towards the lock-loop by contacting metal edge 38, which prevents locking of the matrix on the tooth. However, when as in FIG. 27a, the metal edge 34 ends at line 35, the lock-loop impregnators 90 are activated and matrix is locked, and when the coil is thereby able to bear against said lock-loop without being blocked at point 38 as in FIG. 27.

FIG. 5 shows a still further embodiment of the matrix. In this embodiment the first end 18 is provided with a notch 19 having a curved bottom and a partial recess 54 is formed in the bottom edge of the tail 12. Recess 54 also has an anti-coning effect and notch 19 is curved to better distribute the tearing forces which must be applied to the notch by the heated winding mandril 60.

The lower edge 64 of end 18 in FIG. 5 is also curved until it reaches edge 17 to improve the lower shape of the inner windings of the coil and again to avoid the coning effect. The curved edge 64 also produces a uniform internal diameter for the coil and better assures a proper engagement of the winding tool with the interior of the coil. The recess 54 of FIG. 5, when heat treating the forming coil creates anti-coning deformations in the non-recessed external windings of the wound coil. These deformations or shrinking of these windings are anti-coning.

The end 18 in FIG. 5 can also be provided with a metal laminate up to the dotted line 66 to improve the engagement capability of the first end 18, with the Dentist's winding tool tip 82.

In FIG. 5, the head or second end 20 is provided at the occlusal with a notch 37 and at the gingival with an said extruded aperture 26. The aperture 26 can be thickened in accordance with the embodiments of FIGS. 3, 9 or 10.

Referring now to FIGS. 6 through 8, severable metal lock-loops 24 are shown which each have undulations in a front leg 56 which is meant to extend on the outside of the matrix when it is positioned around the tooth as shown in FIG. 27. An inner leg 58 of the locking loop shown in FIG. 6 is curved outwardly. This improves the engagement and the locking capability of the lock-loop with a plastic material which is softer than the metal from which prior matrices were formed, and requires a convoluted deformation of the plastic band as it passes through the lock-loop and impinges on impregnators 90, as in FIG. 28, to facilitate the positive locking of the lock-loop 24.

In the embodiment of FIG. 8, the lock-loop of FIG. 6 is shown engaged in extruded apertures of FIGS. 1, 3 and 5.

As noted above, FIGS. 9 through 12 show blank sheets from which various embodiments of the invention can be produced. In the embodiment of FIG. 11, a plastic sheet 49 has strips 48 and 51 connected to opposite edges thereof, in which strips 48 overlap the edges only partly to leave a portion of the matrix 48-A of FIGS. 11 and 12 which is made only of metal, and therefore, more readily engagable by said heated coiling mandril 60 of FIG. 18, and is a more springlike coil core for disengagement of winder tip 82, when the winder is wound reversely. The foregoing, partial metal overlap, also applies to FIG. 12.

FIG. 13 shows the tail portion 12 of an embodiment of the invention which is made entirely or substantially entirely of plastic. Notch 19 has a curved bottom and end 18, made entirely of plastic, has a staircased set of ridges or teeth 70. Said steps 70 provide readily engagable right angles to the teeth of the winding tool on the front edge of the end 18 to ensure proper engagement for the winding of the coil by the Dentist's winding tool 82. FIG. 13 also illustrates the use of slits 72 near the end of tail 12 which help form a polygonal shape to the interior windings of the coil as illustrated in FIG. 16. This has been found to better stabilize the coil inside dimensions and provide a predictable internal diameter for the coil. FIG. 16 also illustrates a hot air blow tube 74 which can be used to blow forced hot air onto the exterior of the coil for setting the windings of the plastic of the coil by a partial melting of it and thereby cause coil to retain its shape, and dimensions.

Another way of heating the coil is by heating the mandril 60 shown in FIG. 18 or by providing a heated partial sleeve 76 of FIG. 17 which is provided with heat through a tube 77. FIG. 18a shows heated mandril 60 forming coil 22.

It is noted that the steps or ridges 70 can be used with or without the slits 72 and that the head (not shown in FIG. 13) can be of varied design, for example corresponding to the heads of FIGS. 1, 4 or 5.

FIG. 14 shows another embodiment of the invention wherein a metal clip of staple like wire 78 is fastened to the end 18 of the tail 12. As shown in FIG. 15, ends of the wire clip extend through openings in tail end 18 in the plastic matrix material. Said wire clip 78, provides a leading edge inside said formed coil core for ready windable engagement by the Dentist's winding tool tip 82. FIG. 14a, is a coiled view of FIG. 14.

FIG. 17 illustrates a winding coil 22 which has been heated by the partial sleeve 76. FIG. 17 also shows the use of dimples 80 developed by applied heat near the bottom of gingival edge of the coil 22. This has been found to reduce the coning effect. This effect is illustrated in FIG. 19 as noted above. The dimpling can be achieved by providing a type of plastic which is work handenable, and which is effected by heat so that it tends to retain the shape in which it is deformed, by positive contact to the coils occlusal edge during the heated coil-forming process.

In some situations the coil may be treated in other manners to retain its coiled dimension, such as for example, by using an adhesive that would allow unwinding and rewinding as required in using the dental matrix.

It is also noted that in all of the previous embodiments, the plastic portions can be made either of opaque or transparent plastic. However transparent plastic is required for light curable restorative materials, since it permits transmission of light to facilitate the cure and setting of said light curable restorative material.

FIG. 18a shows a heated coil forming mandril 60, in process of transmitting the heat to the core of the coil 22. An alluminum alloyed mandril will readily transmit the heat to the core of the coil.

FIG. 20 shows the winding end or head 82 of a winding tool. The shank 84 of the winding tool is provided with a shoulder 86 having a larger diameter than the outer diameter of a winding coil 22. This prevents the winding head 82 from being pushed too deeply into the center of the coil to produce the coning effect shown in FIG. 19. FIG. 20 also illustrates a modified Dentist's winding head having a smooth portion 88 which has no teeth. This facilitates easy entry of Dentist's winding tool 82 into coil 22.

FIG. 21 illustrates a modified form of the Dentist's winding head 82 which includes an O-ring 91 on the shank 84. This has the same purpose as the shoulder 86 in FIG. 20. Ring 91 can be made of elastic material and be in the from of a small O-ring which can be slipped over the winding head and onto the shank.

FIG. 21a is a cross sectioned view of coil 22, showing engaging edge 17, internally exposed in coil core for engagement by Dentist's winding tool tip 82, also shown, is anti-coning concavity resulting from gingival recess 32, more readily seen in FIG. 1.

FIG. 22 illustrates an A-symmetrical winding mandril 74 which has a slot 66 that is offset with respect to a center of the mandril as shown in FIG. 24. This produces an off centered cross-hair 79 in the core of the coil shown in FIG. 23. This is particularly useful when using an all plastic coil since it provides the Dentist's winding tool 82 with a prominent engagable leading edge 29.

FIG. 25 illustrates another embodiment of the matrix wherein the tail 12 tapers in width toward the end 18. This is another mechanism for reducing the telescopic coning effect. FIG. 26 shows another form of the invention similar to that of FIG. 25 but wherein the end 18 includes a winding notch 19. Tail 12 may be coiled with either heated mandril 60 or 74.

As shown in FIGS. 27 and 28, the matrix can be slipped over a tooth 94 to be restored. Tooth 94 is shown from gingival view point. The head 82 of a winding tool is then inserted into the winding coil 22 and the winding coil 22 is rotated until the coil bears against the locking loop 24 so as to activate lock-loop impregnators 90 as in FIGS. 6, 8 and 28. It is noted that this occurs automatically at the precise time when the coil draws off all surplus band material from around the tooth, which is a function of the increasing size of coil which activates the lock-loop. When the coil has drawn off all surplus banding material from around the tooth, band 16 becomes taut and impregnates itself onto impregnators 90. The top or occlusal portion of the lock-loop is severed by the Dentist so as to open the matrix after the restorative material is cured. In the stainless steel locking loop of the prior art, a force of between seven and a half and nine inch-ounces of torque was required of Dentist's winding tool to properly activate the pressure of the coil against the lock-loop. It has been found that with the present plastic matrix invention, less torque is required to adapt the soft plastic to the tooth. About four and one half inch ounces of torque is sufficient for activating the impregnators 90. The Dentist's tool which has a setable slip clutch, provides this lower torque so that the coil cannot be unnecessarily overwound. Less torque provides patient's comfort during adaptation of a matrix band.

Once all work has been completed on tooth 94, of FIG. 27a, including the use of the curing light to set a light curable restorative material on the tooth, the plastic matrix is removed by cutting the occlusal end of head 20 as well as the occlusal of lock-loop 24, on the line 96 shown in FIG. 29. FIG. 29 illustrates another advantage of the invention wherein an aperture 26 is used near the gingival edge of the head 20. In this way the gingival portion of the lock-loop is retained in aperture 26. This prevents the remainder of the loop from falling into the patient's mouth when the lock-loop is cut and the matrix is removed. The occlusal half of the loop 24 is captured and retained by a specially designed cutting tool which is known in the art so that no part of the lock-loop is left to fall into the patient's mouth.

While specific embodiments of the invention have been shown and described in detail to illustrate the application of the principles of the invention, it will be understood that the invention may be embodied otherwise without departing from such principles.

What is claimed is:

1. A dental matrix for engaging around a tooth, comprising:
    a plastic blanked sheet member having a straight windable portion carrying a first tail end of said sheet member, an intermediate portion carrying a curved tooth engaging portion carrying a second head end of said sheet member;

said straight windable portion being wound into a cylindrical coil and being heat treated to retain an inside diameter and an outside diameter for said coil, said first end being disposed in a core of said coil;

said curved tooth engaging portion having receiving means at said second head end;

locking means engaged with said receiving means and with said intermediate portion of said sheet member between said coil and said second end to form said curved tooth engaging portion into a tooth engaging band, said locking means permitting a slidable withdrawal of said intermediate portion through said locking means with a winding of said coil with a dentist's matrix coil winder tool for tightening said band around a tooth by winding of said coil against said locking means, which locks the matrix on the tooth; and winder engaging means at said first tail end for engaging a matrix coil winder tool for winding said coil.

2. A dental matrix according to claim 1, wherein said coil includes a plurality of super-imposed windings and has a gingival plane adapted to face a patient's gingiva said matrix including anti-coning means associated with said coil for preventing any of said windings from telescopically moving axially into said gingival plane.

3. A dental matrix according to claim 1, wherein said plastic sheet member is made of transparent plastic.

4. A dental matrix according to claim 1, wherein said plastic sheet member is made of plastic which is work hardenable, and heat formable.

5. A dental matrix according to claim 1, wherein said receiving means comprises at least one extruded aperture on said second head end to be engaged by said locking means comprising a lock-loop having a portion extending through said aperture.

6. A dental matrix according to claim 5, wherein said second head end is made of material which is thicker than a remainder of said plastic sheet member, at least around said aperture.

7. A dental matrix according to claim 5, wherein said second head end is thicker than a remainder of said plastic sheet member only around said aperture.

8. A dental matrix according to claim 1, wherein said head end has at least one aperture whose rim is extruded through a face of said sheet on said second end, to the opposite side of said sheet member, thereby to provide a reinforced protruding edge to said aperture.

9. A dental matrix according to claim 1, wherein said winder engaging means comprises a metal laminate at said first end of said sheet member connected to said straight windable portion.

10. A dental matrix according to claim 9, wherein said metal laminate only partially overlaps said straight winding portion so that at least a terminal portion of said first end is made entirely of metal.

11. A dental matrix according to claim 10, wherein said metal laminate has an edge which extends at at angle to a longitudinal axis of said straight windable portion, said coil comprising a plurality of super-imposed windings, said edge lying on an outer surface of one of said windings.

12. A dental matrix according to claim 11, including a curved recess on an upper edge of said straight windable portion where said edge of said metal laminate meets said edge of said straight windable portion.

13. A dental matrix according to claim 12, wherein said metal laminate has a width which is less than a width of said straight windable portion away from said first tail end thereof.

14. A dental matrix according to claim 1, wherein said receiving means comprises at least one notch, in said head end, and said locking means comprising a lock-loop for engaging said notch, and a metal laminate connected to said second head end of said curved tooth engaging portion, said metal laminate extending only to an intermediate area of said notch.

15. A dental matrix according to claim 1, including a recess in a gingival edge of said straight windable portion adjacent said first tail end for reducing a width of said straight windable portion adjacent said first tail end so that inner portions of said coil will not telescopically project below outer portions of said coil once said coil is engaged by a dentist's winder, with said coil portion being heat treated to grip said narrow width portion to resist said telescopic projection of the cores windings.

16. A dental matrix according to claim 1, wherein said locking means is engagable into said receiving means which comprises a lock-loop having an undulating outer leg and an inner leg, said second end and said intermediate portion of said sheet member lying between said inner and outer legs.

17. A dental matrix according to claim 16, wherein said inner and outer legs are bowed into an arcuate formation to conform more readily to the natural curvature of natural teeth, the better to adapt and lock said matrix to said teeth when the matrix is tightened.

18. A dental matrix according to claim 1, wherein said winder engaging means comprises a terminal edge of said first end including a plurality of stepped ridges, said first end being made entirely of plastic.

19. A dental matrix according to claim 1, including a plurality of spaced slits extending partially edgewise into said straight windable portion adjacent said first end thereof from an occlusal edge of said straight winding portion.

20. A dental matrix according to claim 1, wherein said winder engaging means comprises a metal clip connected to said first tail end of said sheet member, said first tail end of said sheet member being otherwise made of plastic.

21. A dental matrix according to claim 1, wherein said coil includes a plurality of circumferentially spaced dimples at a gingival end thereof.

22. A dental matrix according to claim 1, wherein said straight windable portion tapers in width towards said first end.

23. A dental matrix according to claim 2, wherein said anti-coning means comprises a dentist's winder for engaging said pre-formed coil having a shank with a shoulder having a diameter larger than that of said coil.

24. A dental matrix according to claim 23, wherein said shoulder comprises an O-ring engaged around said shank.

25. A dental matrix according to claim 9, wherein said laminated metal end of said straight windable portion adjacent said first tail end has a notch, said notch extending through a portion of an interior of said cylindrically formed coil.

26. A dental matrix according to claim 25, wherein said notch extends through an interior of said coil away from a center of the interior of said coil.

27. A method of manufacturing a dental matrix having a plastic sheet member with a straight windable portion carrying a first tail end of said blanked sheet member and a curved tooth engaging portion carrying a second head end of said sheet member, comprising:
  winding said straight windable portion into a coil having a selected inside and a selected outside diameter; and
  heating said coil to retain said coil's inside and outside diameters.

28. A method according to claim 27, including forming the coil with a heated mandril having dual diameters along its longitudinal extent, wherein the diameter at the tip of the mandril is smaller than a portion of the mandril away from said tip, which when forming said coil with said heated mandril, the coil core is formed with a dual-diametered anti-coning coil core which resists telescopic movement towards the gingival of the coil's core windings, and stabilizes the coil core diameter for ready engagement of a dentist's winding tool.

29. A method according to claim 27, including forming said first end of said sheet member of metal by attaching a strip of metal to a sheet of plastic material and stamping out said matrix blank from said sheet of plastic material and with said laminated strip of metal.

30. A method according to claim 27, including forming said second head end of thicker material than a remainder of said curved tooth engaging portion and said straight winding portion.

31. A method according to claim 27, including forming an aperture through said second end in a plastic matrix in such a way so that the edges of the rim of said aperture are extruded and rolled into said aperture with the edges of said aperture being projected through said aperture to the opposite side of said aperture resulting in a rolled, thicker edge to said aperture to resist thereby the shearing forces of a lock-loop against said extruded lock-loop engagable aperture.

32. A dental matrix for engaging around a tooth comprising:
  an intermediate plastic band portion;
  coiling means at one end of said intermediate plastic band for tightening said portion against said tooth; and
  means for adjustably retaining said coiling means in a coiled mode of varying magnitude.

33. The dental matrix of claim 32 wherein said means for adjustably retaining said coiling means in a coiled mode of varying magnitude is a pressure sensitive adhesive and facing release surface.

* * * * *